United States Patent [19]

Wadsworth

[11] 4,378,607
[45] Apr. 5, 1983

[54] ELBOW REPLACEMENT PROSTHESIS

[76] Inventor: Thomas G. Wadsworth, 22 Hyde Park Sq., London W2 2NL, England

[21] Appl. No.: 210,297

[22] Filed: Nov. 26, 1980

Related U.S. Application Data

[63] Continuation-in-part of Ser. No. 931,319, Aug. 7, 1978, abandoned.

[30] Foreign Application Priority Data

May 31, 1978 [GB] United Kingdom ............... 25112/78

[51] Int. Cl.³ .............................................. A61F 1/03
[52] U.S. Cl. ..................................... 3/1.91; 128/92 C
[58] Field of Search ......................... 3/1.9, 1.91, 1.911; 128/92 C

[56] References Cited

U.S. PATENT DOCUMENTS

| D. 245,259 | 8/1977 | Shen | 3/1.91 X |
|---|---|---|---|
| 3,547,115 | 12/1970 | Stevens | 3/1.91 X |
| 3,708,805 | 1/1973 | Scales et al. | 3/1.91 |
| 3,728,742 | 4/1973 | Averill et al. | 3/1.911 |
| 3,813,700 | 6/1974 | Tavernetti et al. | 3/1.911 |
| 3,816,854 | 6/1974 | Schlein | 3/1.91 |
| 3,852,831 | 12/1974 | Dee | 3/1.91 |
| 3,919,725 | 11/1975 | Swanson et al. | 3/1.91 |
| 3,922,726 | 12/1975 | Trentani et al. | 3/1.912 |
| 3,990,117 | 11/1976 | Pritchard et al. | 3/1.91 |
| 4,003,096 | 1/1977 | Frey | 3/1.91 |
| 4,008,495 | 2/1977 | Cavendish et al. | 3/1.91 |
| 4,038,704 | 8/1977 | Ring | 3/1.91 |
| 4,057,858 | 11/1977 | Helfet | 3/1.91 |
| 4,131,956 | 1/1979 | Treace | 3/1.91 |
| 4,134,158 | 1/1979 | Laure | 128/92 C X |
| 4,135,517 | 1/1979 | Reale | 3/1.913 X |

FOREIGN PATENT DOCUMENTS 1444724 8/1976 United Kingdom ................... 3/1.91

Primary Examiner—Clifford D. Crowder
Attorney, Agent, or Firm—Carroll F. Palmer

[57] ABSTRACT

Prosthetic replacement of an elbow joint is accomplished using a humeral component having an articular surface comprising a concave surface in the coronal plane and a convex surface in the sagittal plane with such component being cemented along a superior U-slot to a surgically prepared humeral bone. The prosthesis also comprises an ulnar component having an articular surface defined by a convex surface in the coronal plane and a concave surface in the sagittal plane, its undersurface having a longitudinal arcuate keel and a dependent stem by which it is cemented to the surgically prepared ulnar bone. Optionally, the prosthesis may include a radial head component in the form of a dished button that can be cemented to the surgically prepared radial bone by a depending stem.

10 Claims, 18 Drawing Figures

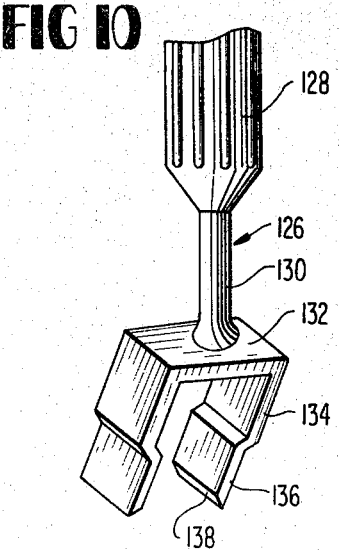
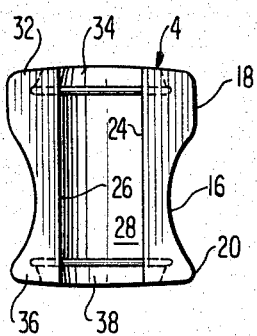
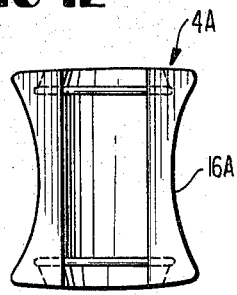
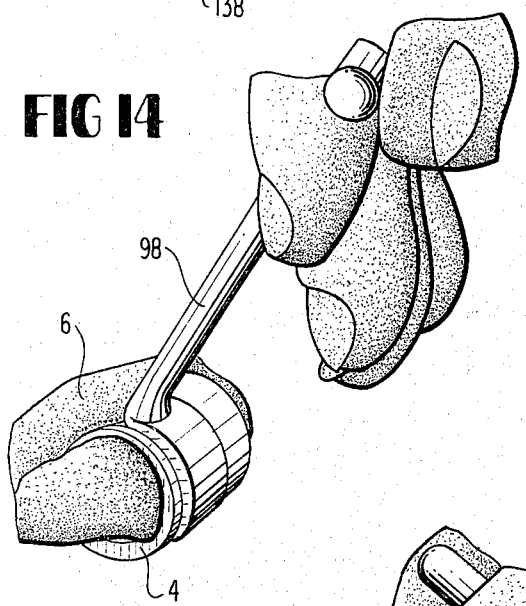
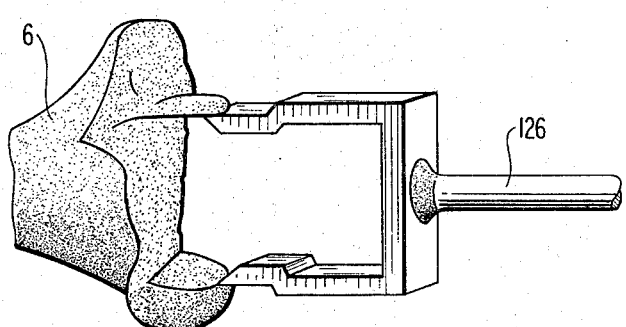
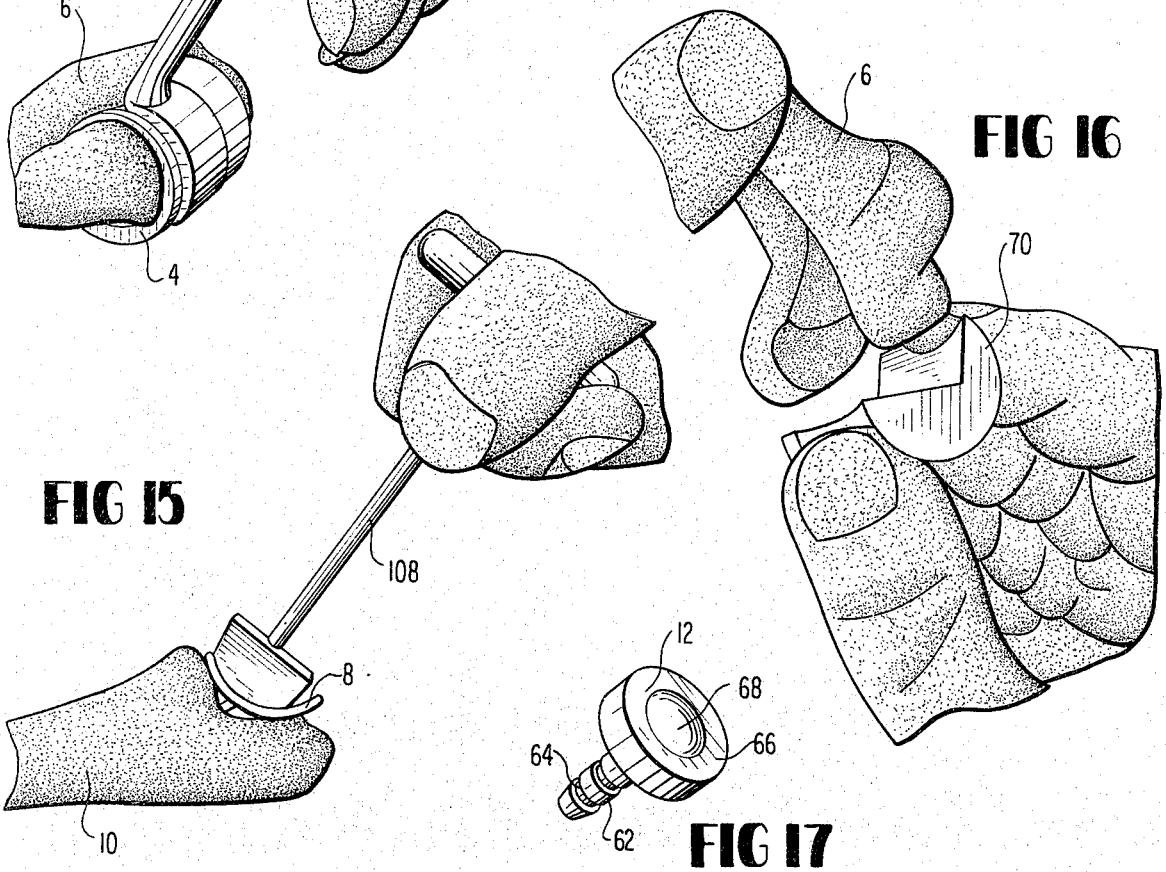
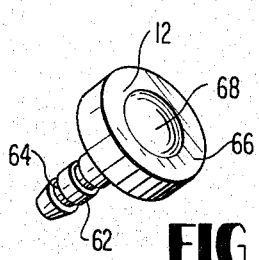

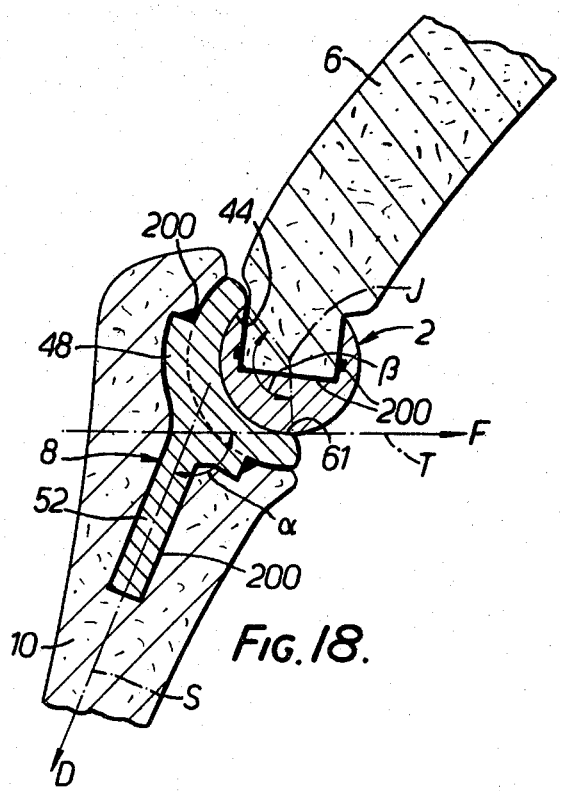

ELBOW REPLACEMENT PROSTHESIS

CROSS-REFERENCE TO RELATED APPLICATION

This application is a continuation-in-part of co-pending application Ser. No. 931,319, filed Aug. 7, 1978 now abandoned.

BACKGROUND OF THE INVENTION

1. Field of the Invention

This invention relates to a prosthesis for replacement of arthritic or damaged elbow joints. More particularly, it concerns a form of elbow joint prosthesis that has good joint stability with minimum bone removal while providing normal flexion and extension motion; there is no in-built constraint and little strain on the seating of the prosthesis.

2. Description of the Prior Art

In general, prosthetic replacement of the elbow has proved a difficult and often disappointing task over the years and this has been the experience of most surgeons in this field. In the past, it was common to replace the elbow joint by means of a constrained prosthesis, usually consisting of a large stem inserted into the humerus and another into the ulna and the two parts of the component linked together by an axle pin. The strong forces on the elbow tend to disrupt the prosthesis from the bone and a very great deal of bone had to be removed to put in such a prosthesis, resulting in the long-term in a disastrous situation very often if the prosthesis has, in fact, to be removed.

There has been a move in recent times to surface replacement of the elbow joint and my work in this area led to the development of a constrained device with a T-slot stability factor which is described in U.S. Pat. No. 4,079,469. Numerous other patents have issued describing bone joint prostheses of which the following is a representative listing:

U.S. Pat. Nos. 2,784,416; 3,547,115; 3,748,662; 3,798,679; 3,801,990; 3,816,854; 3,840,905; 3,852,831; 3,869,729; 3,886,599; 3,919,725; 3,990,116; 4,038,704; 4,057,858; and United Kingdom Pat. No. 1,444,724.

U.S. Pat. No. 3,852,831 describes an endoprosthetic elbow joint having an ulnar component with a saddle shaped bearing surface and a humeral component including a bifurcated member supporting a bearing member between the free ends of its arms. The humeral bearing member has a bearing surface which is arranged to engage in and across the saddle shaping of the ulnar component for mutual articulation. In a preferred arrangement the ulnar component includes a platform with which a bearing member is releasably connected suitably by a sliding dovetail-section keying, the connecting interfaces are circularly curved, and the bearing member can pass through the humeral component. With this arrangement the humeral component and ulnar platform are fixed in place and the ulnar bearing member is then passed through the humeral component in bearing engagement therewith to connect with the platform.

U.S. Pat. No. 4,038,704 discloses an elbow prosthesis comprising a humeral component and an ulnar component, in which each component comprises a joint portion for forming the joint of the prosthesis and an implant portion for implantation into the bone, the joint portion of the humeral component being capable of being received by the joint portion of the ulnar component in snap-fit engagement, while permitting the humeral component to pivot relative to the ulnar component. In order to achieve the snap-fit engagement between the humeral component and the ulnar component, the articular surface of the ulnar component subtends more than 180° at the axis of turning of the prosthesis.

U.S. Pat. No. 4,057,858 discloses an elbow prosthesis including humeral and ulnar components in which the head of the humeral component has a convex medial condylar formation presenting a smooth curved trochlear groove in the shape of part of a helix and providing a bearing surface for a head of the ulnar component and in which the ulnar component presents a condylar head contoured to fit into the trochlear groove, so that as the ulnar component turns around the humeral component, with the condylar head mating with the trochlear groove, the ulnar component moves along the pivotal axis and the ulnar performs the required valgus in extension and varus in flexion. Thus, the humeral articulation groove is in the shape of part of a helix, in order that the elbow adopts a valgus position in extension and a varus position in flexion. However, patients vary in that some have a valgus angle in extension of the elbow, some, but fewer, have a varus angle in extension, and others are between the two, namely having substantially zero angle in extension. This prosthesis, in being designed for a valgus angle in extension cannot cope with the whole range, without serious risk of displacement.

U.S. Pat. No. 3,547,115 describes an osteoarticular prosthesis and prosthetic method which is particularly adapted for use on the distal humerus. The prosthesis has an outer articular surface corresponding to the articular surface being replaced. The bone upon which the prosthesis is to be mounted is preferably first trimmed to fit a keyhole-type opening in the prosthesis. The prosthesis has a sharpened leading edge and is transversely driven onto the bone. Once in place, the prosthesis is locked against displacement by its keyhole-type interengagement with the bone. Consequently, the articular surface of the prosthesis includes a part-spherical capitellum. Naturally, the maximum radius of the capitellum relative to the axis of the joint is determined by the radius bone or radial component with which the capitellum co-operates. Since the articular surface of the humeral component co-operating with the ulna or ulnar component terminates at one axial end adjacent to this part-spherical capitellum, the radius of that one axial end is less than the maximum radius of the capitellum. Therefore, this one axial end presents a low obstruction to lateral displacement of the ulna or ulnar component relative to the humeral component in the direction of the capitellum.

Similar comments apply in respect of U.S. Pat. No. 3,919,725, which discloses an endoprosthetic elbow joint comprising humeral and ulnar components which are each of trough form. The humeral component outer surface is of circular cylindrical form over at least part of its length and is secured to the humerus at its inner surface, while the ulnar component has a complementary circular cylindrical inner surface for mutually articulatory bearing engagement with the humeral component and is secured to the ulna at its outer surface. In a modification the humeral component has a convex, part-annular, part-spherically shaped extension to its outer surface, which extension articulates with a complementary concave surface of an additional component for securement to the radius.

Various ways are known of fixing a plastics prosthetic articular head to a metal prosthetic stem. For example, U.S. Pat. No. 3,816,854 dislcoses a humeral component consisting of a generally cylindrical head of ultra high density polyethylene and a chrome-nickel-cobalt alloy stem incorporating at its distal end a hollow partial cylinder which closely embraces the head. Shallow protruberances on the inner surface of the partial cylinder engage in shallow depressions in the outer surface of the head to retain the head on the stem. U.S. Pat. No. 4,131,956 describes a humeral component consisting of a generally cylindrical internally threaded head of a biocompatible plastics, a forked stem of biocompatible metal, and two screws screwed into the threaded interior of the head through the respective limbs of the fork of the stem.

In spite of the numerous procedures and devices previously developed and used for elbow reconstruction, there exists a need for further improvement particularly as regards resulting joint stability, minimal removal of bone for insertion and allowance for normal flexion and extension motion as well as minimal strain on the seating of the prosthesis.

OBJECTS

A principal object of the present invention is the provision of new forms of bone joint prosthesis.

Another object is the provision of a type of elbow prosthesis that is characterised by:

(i) Minimal removal of bone for insertion.

(ii) Protection of the ulnar nerve within the cubital tunnel by preservation of the medial lip of the trochlea.

(iii) Allowance for normal flexion and extension motion at the elbow.

(iv) Stability, which is importantly achieved by the arrangement of the joint articulation that guards against undue medial and lateral movement which would be abnormal for the elbow.

(v) Additional overall stability that ensues from minimal interference with ligaments and capsule associated with the operative technique.

(vi) Lightness in weight.

(vii) Relatively inexpensive to produce.

(viii) Should removal of the implant be necessary, e.g., for infection, the patient would be left with a conventional *excision arthroplasty* which should give useful function.

A further object is the provision of an elbow prosthesis useful in rehabilitating a patient with a severe arthritic problem of the elbow and which may be easily inserted by any orthopaedic surgeon.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished by the following and other aspects of the present invention.

According to one aspect of the present invention, there is provided an elbow replacement prosthesis comprising:

a humeral component having an articular surface that is curved concave in a coronal plane and curved convex in a sagittal plane, an articulate ulnar component having an articular surface that is curved convex in a coronal plane and curved concave in a sagittal plane complementary to said articular surface of said humeral component and has a distal end and a proximal end, said articular surfaces of said humeral component and said ulnar component being substantially symmetrical about a plane perpendicular to the axis of turning of the prosthesis, and said ulnar component has a stem extending therefrom opposite to said articular surface of said ulnar component and the angle between the forward direction of the tangent to the distal end of such articular surface and the distal direction of the longitudinal axis of said stem is more than 90°, and the articular surface of the ulnar component subtends at said axis of turning an angle of less than 180°.

Having the forward direction of the tangent to the distal end of the articular surface of the ulnar component at an angle of more than 90 degrees to the distal direction of the stem of the ulnar component, but without any snap-fit engagement between the components, has the advantage that forces in the proximal direction of that stem, which are common in normal use of the joint, do not tend to dislocate the ulnar component posteriorly relative to the humeral component. The risk of such dislocation is an important hazard in elbow replacement surgery and is greatly discouraged by this novel feature.

Moreover, the fact that the articular surfaces are complementary gives good stability to the joint. Because the articular surfaces are of curved convex and curved concave form a reasonable amount of tolerance in positioning of the components in the bones is allowable. Furthermore, because the articular surfaces are both symmetrical about a plane perpendicular to the axis of hinging of the prosthesis, the prosthesis can cope with all of the range of angle in extension of the elbow, from a valgus angle to a varus angle, which is particularly advantageous in arthritic patients.

According to a second aspect of the present invention, there is provided an elbow replacement prosthesis comprising:

an arcuate ulnar component having an articular bearing surface and, opposite said surface, an arcuate keel extending therealong with the arcuate curvature of said keel being similar to that of said ulnar component, and a stem depending from said keel, the dimension of said keel in a coronal plane being substantially less than that of said bearing surface.

Since the articular surface of the olecranon process of the ulna naturally has an arcuate curvature, the making of the keel arcuate minimises the amount of bone needing to be removed, although it is normally necessary to remove an arcuate segment of that surface in order to receive the arcuate keel. Minimizing of bone removal is also promoted by the fact that the radially outer surface of the arcuate articular portion of the ulnar component bears substantially face-to-face on the articular surface of the olecranon. Further minimising of bone removal can be achieved by ensuring that the dimension of that arcuate articular portion radially of the joint is as small as is practicable.

According to a third aspect of the present invention, there is provided an elbow replacement prosthesis comprising:

a humeral component having an articular surface that is curved concave in a coronal plane and curved convex in a sagittal plane, an arcuate ulnar component having an articular surface that is curved convex in a coronal plane and curved concave in a sagittal plane complementary to said articular surface of said humeral component, said articular surfaces of said humeral component and said ulnar component being substantially symmetrical about a plane perpendicular to the axis of turning of the prosthesis, and said humeral component comprises a substantially cylindrical surface arranged laterally beyond the articular surface of said humeral component for cooperating with the radius bone or a radial component.

Since the articular surface of the humeral component at one axial end terminates adjacent to a substantially cylindrical capitellum, then the radius of the articular surface at that one axial end can be substantially equal to the maximum radius of the capitellum. This has the advantage that this one axial end provides a high obstruction to lateral displacement of the ulnar component relative to the humeral component in the direction of the capitellum.

According to a fourth aspect of the present invention, there is provided a prosthetic component comprising an articular head, a first hole of closed cross-section extending in said head from a first surface zone of said head, a second hole of closed cross-section extending in said head from a second surface zone of said head and joining said first hole, a stem extending along said second hole and formed with an aperture therethrough aligned with said first hole, and a member extending in said first hole and said aperture and retaining said head on said stem.

Thereby, not only can the head be reliably retained on the stem, but the amount of bone needing to be removed can be minimal.

BRIEF DESCRIPTION OF THE DRAWINGS

A more complete understanding of the new elbow replacement prosthesis of the invention may be had by reference to the accompanying drawings in which:

FIG. 10 is a perspective view of another chisel used in implanting the humeral component.

FIG. 11 is a plan view of the usual form of humeral component of the new prosthesis.

FIG. 12 is a plan view of the special form of humeral component used for replacement of a totally destroyed elbow joint.

FIG. 13 is a fragmentary perspective view of a chisel cutting the humerus for implantation of the humeral component.

FIG. 14 is a fragmentary perspective view of a humeral impactor pushing the humeral component onto the humeral bone during cementing.

FIG. 15 is a fragmentary perspective view of an ulnar impactor pushing the ulnar component onto the ulnar bone during cementing.

FIG. 16 is a fragmentary perspective view of a trial humeral component being applied to the humerus.

FIG. 17 is a perspective view of a radial head component that may be used on occasion in the new elbow replacement prosthesis.

FIG. 18 is a sectional view taken on the line A—A of FIG. 1.

DESCRIPTION OF THE PREFERRED EMBODIMENT

Figure 1:
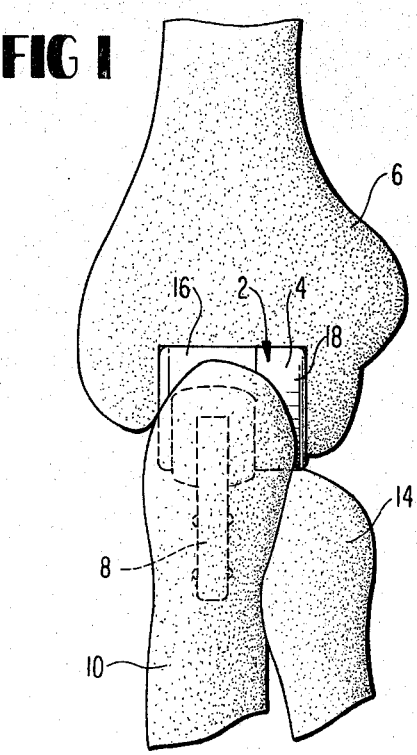
FIG. 1 is a fragmentary anterior elevation of an elbow prosthesis of the invention illustrated as implanted in the humerus and ulna.
Figure 2:
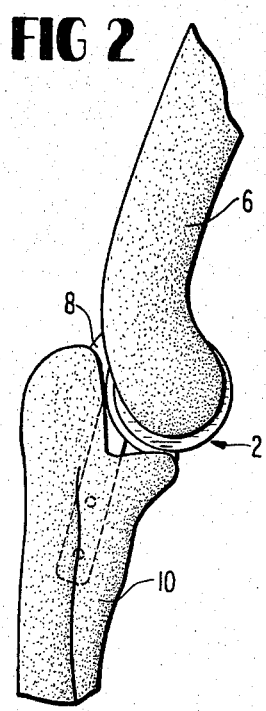
FIG. 2 is a fragmentary lateral elevation of the elbow prosthesis with humerus and ulna in extension position (20°).
Figure 3:
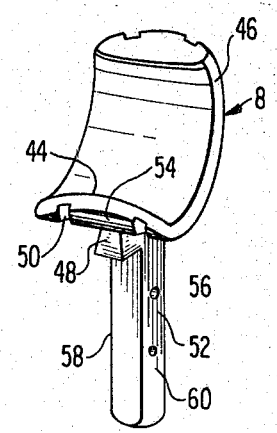
FIG. 3 is a perspective view of an ulnar component of the prosthesis.
Figure 4:
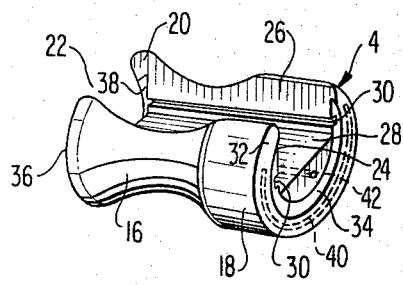
FIG. 4 is a perspective view of a humeral component of the prosthesis.

Referring in detail to the drawings, the elbow replacement prosthesis 2 basically comprises a humeral component 4 that is implanted in the humerus 6 and an ulnar component 8 implanted in the ulna 10. Optionally, it may comprise a radial component 12 (FIG. 17) that is implanted in the radius 14.

The humeral component 4 has a surface 16 which is concave in the coronal plane and convex in the sagittal plane and which at its lateral end merges into a cylindrical surface 18, the latter partially replacing the capitulum bone of the humerus upon implantation. At its medial end the surface 16 merges into a convex surface 20. The surfaces 16, 18 and 20 form the articular surfaces of the humeral component 4 relative to the ulnar component and the radial component.

A slightly different form of humeral component 4A is used in the prosthesis for replacement of a totally destroyed elbow joint (see FIG. 12). The component 4A is the same in all particulars to component 4 except that the articular surface 16A concave in the coronal plane extends right across the whole length of the component 4A and there is no cylindrical surface such as surface 18 in component 4.

The surface for attaching the humeral component 4 to the humerus comprises a superior U-slot 22 with chordal anterior wall 24, posterior wall 26 and flat floor 28. Longitudinal grooves 30 are formed in the walls 24 and 26 for keying of cement for implantation of the component 4. The lateral wall 32 has a peripheral groove 34 and the medial wall 36 a similar groove 38 for keying of cement. Annular wire markers 40 are imbedded in the walls 32 and 26 and a longitudinal wire marker 42 is embedded in the floor 28 so that position of the prosthesis can be determined by X-ray inspection, after implantation, of both the coronal and sagittal planes by means of the three markers.

The main articulating surface of component 4 describes a gently concave curve in the coronal plane which allows for simple and effective engagement with the convex surface 44 in the coronal plane of the ulnar component 8. Thus, a limited amount of sideway rotation motion is allowed which may at times become necessary in order to avoid undue strain on the bony attachments to the prosthetic components.

In the sagittal plane of the component 4, the convex articulating surface 16 increases in radius from its center in both the medial and lateral directions to a similar extent where the surfaces 18 and 20 take over.

The articular surface 44 of ulnar component 8 allows for accurate and easy articulation with surface 16 of the humeral component 4.

The bone attaching portion of the ulnar component 8 comprises a longitudinal, arcuate keel 48 with grooves 50 running longitudinally along beside the keel 48 for keying of cement in implantation. The keel 48 depends from the undersurface 54 of the arcuate articulating portion of the component 8 and has a dovetailed cross-section in the coronal plane. A stem 52 depends from the keel 48 for insertion into the ulna. The stem 52 has nipples 56 on both the medial surface 58 and lateral surface 60 for keying into cement for implantation.

The orientation of the stem 52 relative to the articular surface of the ulnar component is selected to control anteversion seating of the component 8 in the ulnar bone 10. With reference to FIG. 18, the angle $\alpha$ between the forward direction F of the tangent T to the distal end 61 of the articular surface 44 of the ulnar component 8 and the distal direction D of the longitudinal axis S of the stem 52 is more than 90°. Hence the distal end 61 of the articular surface of the ulnar component is inclined forwardly generally in the direction F at an angle of more than 90° to the distal direction D of the stem 52. The advantage of this feature is that forces in the direction 180° to the direction D, which are common in normal use of the joint, do not tend to dislocate the ulnar component posteriorly relative to the humeral component. The risk of such dislocation is an important hazard in elbow replacement surgery and is greatly mitigated by this feature of the new prothesis. FIG. 18 also shows that the articular surface of the ulnar component 8 subtends at the axis J of the turning of the joint an angle $\beta$ of less than 180°. The advantage of this feature is that if the joint should become dislocated the two components will not be prevented from returning to a proper position with their respective articular surfaces in contact with one another. Cement between each component and the ulna 10 or the humerus 6 is indicated in FIG. 18 by the solid shading 200.

Making the capitellum surface 18 cylindrical has the advantage that the merging lateral end of the surface 16 provides a high obstruction to lateral displacement of the component 8 relative to the humeral component.

A reconstructed elbow joint according to the invention may also include a radial component 12 (FIG. 17). In actual fact, although the head of the radius 14 is always removed for insertion of the prosthesis, it is not always necessary to replace this removed bone. However, in necessary cases, the bone may be replaced with the radial component 12 which comprises a distal key portion 62 having cement keying grooves 64 and an integral proximal bearing button 66 with dished surface 68. If the component 12 is used, it is implanted into the surgically prepared radius 14 and fixed in place with cement in a manner similar to implant of the ulnar component 8.

In order to assess the depth of humeral bone to be removed and also for sizing of a component to fit a particular patient, trial humeral components may be used, i.e., special component 70 or usual humeral component 72. The component 70 corresponds to the permanent special component 4A and component 72 to the permanent usual component 4.

The component 70 comprises the concave surface 74 in the coronal plane, lateral wall 76 and medial wall 78. Instead of a U-shaped slot as in the permanent component 4A, component 70 has an L-shaped slot defined by the posterior wall 80 and the floor 82.

The component 72 comprises the concave surface 84 in the coronal plane, convex surfaces 86 and 88, medial wall 90, lateral wall 92 and an L-shaped slot defined by posterior wall 94 and floor 96.

The components 70 and 72, unlike their permanent counterparts 4 and 4A do not include wire markers or keying grooves, but, aside from this and the L-shaped slots, components 70 and 72 are the same as 4A and 4.

In reconstruction of an elbow joint, only one style of components 4, 4A or 70 need be used. However, with component 72, right and left hand styles must be used dependent upon whether a right or left elbow is being reconstructed.

A variety of materials are available from which to construct components 4, 8 and 12. Advantageously, the humeral component is formed of inert plastic, e.g. high density polyethylene, and the ulnar component 8 and radial component 12 are made of corrosion-resistant metal, e.g., the chromium alloy "Aluvium". The impactors and chisels are advantageously formed of stainless steel or equivalent metal except for the end of the ulnar impactor in contact with the ulnar prosthesis.

The design of the components 4 and 8 as described enables them to be made and used in an average size adaptable to a large number of patients. However, it should be recognised that different sizes may be necessary and this can be determined by use of sized trial components 70 or 72.

Figure 5:
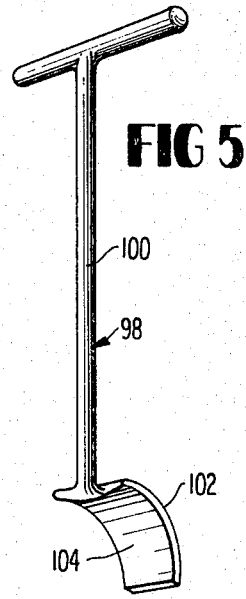
FIG. 5 is a perspective view of a humeral component impactor.
Figure 6:
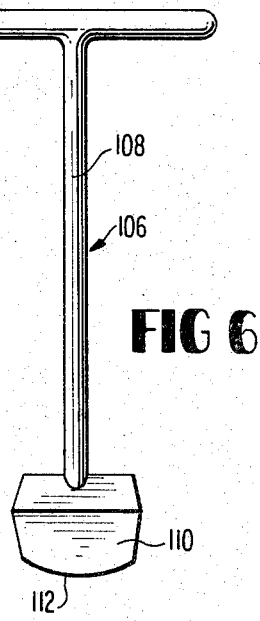
FIG. 6 is a perspective view of an ulnar component impactor.
Figure 7:
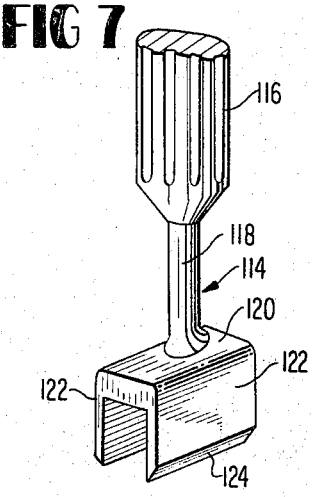
FIG. 7 is a perspective view of a chisel used to cut the humerus for implanting the humeral component.
Figure 8:
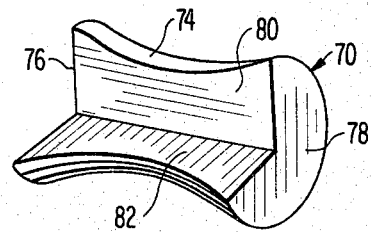
FIG. 8 is a perspective view of one embodiment of a trial humeral component used primarily for replacement of a totally destroyed elbow joint.
Figure 9:
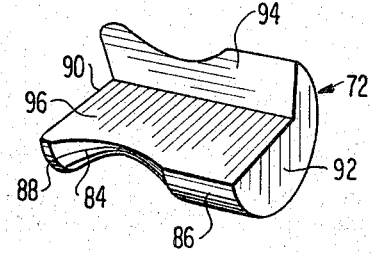
FIG. 9 is a perspective view of another embodiment of a trial humeral component.

Instrumentation for reconstruction of an elbow joint in accordance with the invention is shown in FIGS. 5–7 and 10.

The humeral impactors 98 (or pusher) comprises a T-shaped handle 100 fixed in the coronal plane to the integral distal end member 102 having its pushing surface 104 formed complimentarily to the concave-convex surface 16 of component 4 or 300. This enables impactor 98 to be put in position upon the humeral component easily and be held there accurately while cement hardens during implantation.

The ulnar impactor 106 also has a T-shaped handle 108, but this is fixed in the sagittal plane to the integral distal end member 110. The pushing surface 112 is formed complimentarily to the articulating surface 44 of component 8 to again provide easy placement and accurate holding during cementing.

Chisel 114 comprises mallet head 116, stem 118, base member 120 and two wings 122, each with chisel tips 124. The stem 118 is perpendicular to the base member 120, but offset from the center thereof for ease of access to the elbow joint. Chisel 114 is used to mark out the antero-posterior breadth of the humeral bone to be removed in order to fit into the slot 22 of component 4. It also marks the depth: equivalent to that of the depth of the slot 22 in component 4.

Chisel 126 comprises mallet head 128, stem 130, base member 132, wings 134 with inset ends 136 and chisel tips 138. The wings 134 are in a different plane from the wings 122 of chisel 114.

Chisel 126 is used for accurately marking out the length of humeral bone to be removed and also to mark the depth since the inset ends 136 of the chisel are sized in length to compare with the depth of the body of component 4. Use of chisel 126 to mark out and cut away humeral bone from the humerus 6 is shown in FIG. 13. Chisel 114 is then used in the opposite plane to mark out the antero-posterior breadth of bone removal. Upon completion of humeral bone removal in such manner, the humeral component 4, with cement applied to the surfaces of slot 22 is applied to the humerus 6 and held in place with impactor 98 as shown in FIG. 14 until the cement has set. The keel of the prepared humeral bone sits in the U-slot of component 4 and its medial and lateral ends sit against the medial and lateral walls of the prepared lower humerus.

The ulna is prepared to receive the stem 52 of ulnar component 8. Cement is then applied to the stem 52 and undersurface 54 and the component 8 is inserted into and onto the upper end of the ulna 10. The component 8 is held in position as shown in FIG. 15 with impactor 108 until the cement is fully set. In the reconstructed joint, the ulnar component sits on the olecranon process of the ulnar bone and the stem 52 seats within that bone to give good stability to the component 8.

A preferred cement for use in the new joint reconstructions is self-hardening methyl methacrylate cement, but other body compatible cements may be used.

As previously indicated, trial humeral components may be used in order to assess the depth of humeral bone to be removed and also for sizing of a component to fit a particular patient. FIG. 16 illustrates the application of the trial component 70 to the surgically prepared humeral bone 6.

It is to be understood that FIGS. 13–16 are illustrative only and do not attempt to depict the actual appearance of the operations. Obviously, the actual surgical procedures would be conducted under sterile conditions with the surgeon's hands gloved and there would be flesh around the humerus and ulna.

In an elbow joint reconstructed in accordance with the invention, the articulating surfaces, e.g., 16 and 44, fit easily together and give a range of flexible movement between full extension (0°) to flexion position (140°). Stability is provided, in particular, by the intact medial ligament of the elbow and also by the lateral ligament, the anterior and posterior joint capsule and the adjacent musculature. Hence, any tendency for dislocation of the prosthesis is resisted by the natural anatomy and any lateral shift of the ulna is discouraged by the lateral cylindrical part 18 of the humeral component 4. This is useful if trauma or undue strain is delivered to the elbow joint. Further, the prosthetic articulating arrangement allows for rotation of the ulna at the elbow, thus avoiding strain on the seating of the two components in strain situations.

Minimal bone is removed in the operative procedure which is a distinct advantage if there should be failure of the prosthesis for any reason, in which event, other surgical procedures can be easily accomplished.

The humeral wire markers allow for accurate visualization of the prosthesis by X-ray which is important in assessing wear and/or displacement after accidental trauma or loosening of the humeral component for any reason.

The embodiments of the invention in which an exclusive property or privilege is claimed are defined as follows:

1. An elbow replacement prosthesis comprising:
a humeral component having an articular surface that is curved concave in a coronal plane and curved convex in a sagittal plane, a longitudinal U-shaped slot opposed to said articular surface, said slot being of rectangular section in the sagittal plane defined by a flat floor and parallel anterior and posterior walls, said humeral component further having substantially parallel medial and lateral walls transverse to said slot,
an arcuate ulnar component having an articular surface that is curved convex in a coronal plane and curved concave in a sagittal plane complementary to said articular surface of said humeral component and has a distal end and a proximal end,
said aritcular surfaces of said humeral component and said ulnar component being substantially symmetrical about a plane perpendicular to the axis of turning of the prosthesis,
said ulnar component has a stem extending therefrom opposite to said articular surface of said ulnar component and the angle between the forward direction of the tangent to the distal end of such articular surface and the distal direction of the longitudinal axis of said stem is more than 90°, and the articular surface of the ulnar component subtends at said axis of turning an angle of less than 180°, and
said humeral component has annular grooves in said medial and lateral walls and longitudinal grooves in said anterior and posterior walls to assist in cementing the humeral component in a surgically prepared humeral bone.

2. The prosthesis of claim 1 wherein said humeral component is formed of plastic and said ulnar component is formed of metal.

3. The prosthesis of claim 2 wherein annular metal markers are embedded in said medial and lateral walls and a longitudinal metal marker is embedded in said flat floor.

4. The prosthesis of claim 3 wherein said concave surface of said humeral component ends laterally in convex surfaces.

5. The prosthesis of claim 4 wherein beyond one of said lateral convex surfaces is a cylindrical surface.

6. The prosthesis of claim 1 that includes a radial component having a circular, dished articular surface and a depending stem by which the radial component may be cemented to a surgically prepared radial bone.

7. An elbow replacement prosthesis comprising:
an arcuate ulnar component having an articular bearing surface and, opposite said surface,
an arcuate keel extending therealong with the arcuate curvature of said keel being similar to that of said ulnar component, and
a stem depending from said keel,
the dimension of said keel in a coronal plane being substantially less than that of said bearing surface.

8. The prosthesis of claim 7 wherein said keel has a dovetailed cross-section in the coronal plane.

9. The prosthesis of claim 7 wherein said ulnar component has longitudinal grooves in the surface opposite to its articular surface that run alongside said keel to assist in cementing the ulnar component in a surgically prepared ulnar bone.

10. An elbow replacement prosthesis comprising:
a humeral component having an articular surface that is curved concave in a coronal plane and curved convex in a sagittal plane, an arcuate ulnar component having an articular surface that is curved convex in a coronal plane and curved concave in a sagittal plane complementary to said articular surface of said humeral component, said articular surfaces of said humeral component and said ulnar component being substantially symmetrical about a plane perpendicular to the axis of turning of the prosthesis, and said humeral component comprises a cylindrical surface arranged laterally beyond the articular surface of said humeral component for cooperating with the radius bone or a radial component.

* * * * *